US005113028A

United States Patent [19]

Chen et al.

[11] Patent Number: 5,113,028

[45] Date of Patent: May 12, 1992

[54] PROCESS FOR MIXING ETHANE AND CHLORINE GASES

[76] Inventors: Hang-Chang B. Chen, 138 Daven Dr., Getzville, N.Y. 14068; Gerald F. Achee, 5775 Glenwood Dr., Baton Rouge, La. 70806

[21] Appl. No.: 739,042

[22] Filed: Aug. 1, 1991

[51] Int. Cl.[5] .............................................. C07C 17/00

[52] U.S. Cl. ..................................... 570/255; 570/216; 570/252

[58] Field of Search .................. 48/366; 570/189, 101, 570/159, 181, 186, 216, 234, 252, 255, 190, 241

[56] References Cited

U.S. PATENT DOCUMENTS

| | | | |
|---|---|---|---|
| 2,063,133 | 12/1936 | Tropsch | 568/180 |
| 2,140,547 | 12/1938 | Reilly | 568/180 |
| 2,224,155 | 12/1940 | Kennedy et al. | 568/180 |
| 2,498,552 | 2/1950 | Kilgren et al. | 568/180 |
| 2,628,259 | 2/1953 | Dirstine et al. | 570/255 |

OTHER PUBLICATIONS

Chilton & Genereaux, Trans. Am. Inst. Chem. Engrs., 25, 103 (1930).

L. J. Forney, Jet Injection for Optimum Pipeline Mixing; Ency. Fluid Mech. vil. 2, ch. 25, pp. 660-690, 1986.

Maruyama, et al. Int. Ch. Engr. vol. 23, No. 4 707 (1983).

Maruyama et al., Kagaku Kogaku Ronbunshu, vol. 7, No. 3, pp. 215-221 (1981).

*Primary Examiner*—Werren B. Lone

[57] ABSTRACT

A process for mixing hot ethane with chlorine gas using a mixer consisting of a main pipe through which ethane is conducted, and four or more jets through which chlorine gas is introduced into the main pipe. The angle between the axis of each jet and the line from the center point to the point where the axis of each jet makes contact with the inside surface of the main pipe ranges between about 30° to 45°.

19 Claims, 2 Drawing Sheets

PROCESS FOR MIXING ETHANE AND CHLORINE GASES

BACKGROUND OF THE INVENTION

The present invention relates to a method for rapid mixing of ethane and chlorine gases. More particularly, it relates to a method of mixing hot ethane with chlorine, which gases undergo immediate exothermic chemical reaction upon contact. Several U.S. patents disclose reactions of ethane and chlorine and processes in which the gases must be mixture, for example, U.S. Pat. Nos. 2,259,195; 2,628,259; 2,838,579; and 3,166,601. U.S. Pat. Nos. 2,259,195 and 2,628,259 also disclose the mixing of chlorine with hot ethane. Hot ethane and chlorine react rapidly and exothermically and will form side products such as carbon unless mixing is accomplished quickly. Applicants' invention is useful in that it provides a process for the rapid mixing of hot ethane and chlorine.

The Kirk-Othmer Encyclopedia of Chemical Technology (2nd edition, volume 13, p. 577) indicates that there are several methods of mixing gases. However, they all seem to work by inducing turbulence which causes the gases to mix. Basically, turbulence is induced by causing high velocity streams to collide with each other, or by allowing one stream of gas to expand, through an orifice, into another stream of gas. A mixing tee is a well-known technique for mixing gases. In this technique, a gas flows through a straight pipe, and a second gas is injected at a right angle to the direction of travel of the first gas.

Chilton and Genereaux, Trans. Am. Inst. Chem. End. Grs., 25, 103 (1930), describes their results with such a mixing tee. Although they obtain good results, with non-reactive gases, we were not able to duplicate their results with reactive gases. In Comparative Example 1, results of attempts to mix chlorine with hot ethane are shown. In this system, the reaction begins quickly and is so exothermic that if the mixing is not complete, localized hot spots will result in the formation of carbon. The simple mixing tee did not provide adequate mixing, but instead resulted in a great deal of carbon formation.

L. J. Forney, (*Jet Injection for Optimum Pipeline Mixing*, Encyclopedia of Fluid Mechanics; Cheremisinoff, ed., vol II, Ch. 25, pp. 660–690, Gulf Publishing Company, Houston, 1986), has studied single and dual-jet mixers. One mixer which he studied in detail has two jets on opposite sides of the pipe through which the main stream of gas is flowing. The jets are not directed toward the center of the circle, but rather the angle between the axis of the jet and the radius drawn to the point of entry is 45°. While Forney provides equations to describe mixing, he states that in using the equations, problems can arise when attempting to use the equations to achieve optimum mixing, "particularly when the ratio of jet to pipe diameter is small and the measurement point is less than ten pipe diameters from the injection point." When the gases to be mixed react rapidly, and exothermically, mixing must be accomplished in much quicker than ten pipe diameters if it is to be effective.

As set forth in Comparative Example 1, when hot ethane was mixed with chlorine, carbon deposition due to poor mixing began within two pipe diameters of the mixing point. In other words, if the mixing is not complete within two pipe diameters, problems from side reactions due to poor mixing will occur. Accordingly, the equations of Forney, which are useful at distances of ten pipe diameters from the injection point, are of little help in solving the mixing problem that Applicants face.

Maruyama, Mizushina, and Hayashiguchi, International Chemical Engineering, vol. 23, 707 (1983), studied the optimal conditions for jet mixing in turbulent pipe flow. The apparatus used was described in a prior reference, Toshiro Maruyama, *Kagaku Kogaku Ronbunshu, vol.* 7, no. 3, pp 215–221 (1981). The authors studied both single and dual jet injectors at various angles of injection. In this study, the main pipe has a circular cross-section and the inlet jets are directed at various angles. The angle of injection is defined as the angle between the axis of the inlet jet and the line connecting the point o intersection of the inlet jet access in the inner wall of the main pipe with the center of the main pipe. The authors studied dual jet mixers at 0°, that is, two jets directed directly at each other pointing at the center of the pipe, two jets at angles of $\pi/6$ radians (30°), two jets at injection angles of $\pi/4$ radians (45°), and two jets tangential to the inner walls of the main pipe. They observed that the optimal angle for injection was 30°. However, on page 715, their graphs also indicate that whatever conditions they chose, complete mixing was not obtained in less than five diameters of the main pipe. They also noted that in the case of tangential injection, where the two injection jets could interact, the mixing of the inlet jets with each other suppressed their mixing with the main stream. If tangential mixing is to be employed, the authors state that the velocity ratio of the inlet gas stream to the main gas stream should be lower to prevent the interaction of the two inlet gas streams.

Studies in our laboratory have shown that other methods of mixing gas streams likewise did not serve to mix hot ethane and chlorine. Specifically, we tested coaxial, venturi, fritted disk, and fluidized bed mixers. As set forth in the comparative examples, in each case, carbon formation was a problem. Carbon appears in several forms, including sooty, soft deposits and hard, coal-like deposits. Of course, all carbon formation is undesirable because it represents a loss of starting material. In addition, the fine carbon is a nuisance in handling the gases after mixing. Both the soft deposits and the hard deposits can actually block gas flow in the mixer. The hard carbon deposits are particularly difficult to remove from the mixer.

SUMMARY OF THE INVENTION

Surprisingly, we have now discovered that hot ethane and chlorine gases can be mixed using a mixer containing four or more inlet injectors directed in such a manner that the inlet jet streams are forced to interact with each other.

DETAILED DESCRIPTION OF DRAWINGS

DETAILED DESCRIPTION OF THE INVENTION

Figure 1:
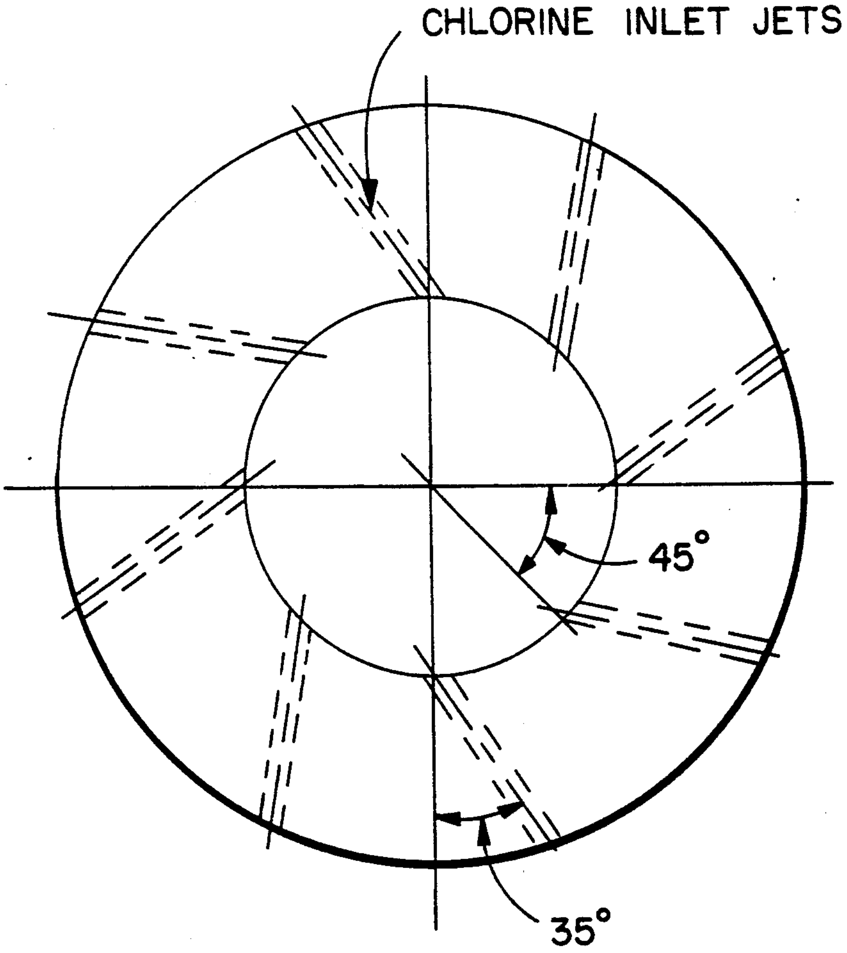
FIG. 1 shows a cross-section of the mixer configured with eight inlet jets with their axes making an angle of 35° with the line drawn from the center point of the main pipe to the point where the axis makes contact with the inside surface of the main pipe. All chlorine jets are in a single plane and the section contains that plane.
Figure 2:
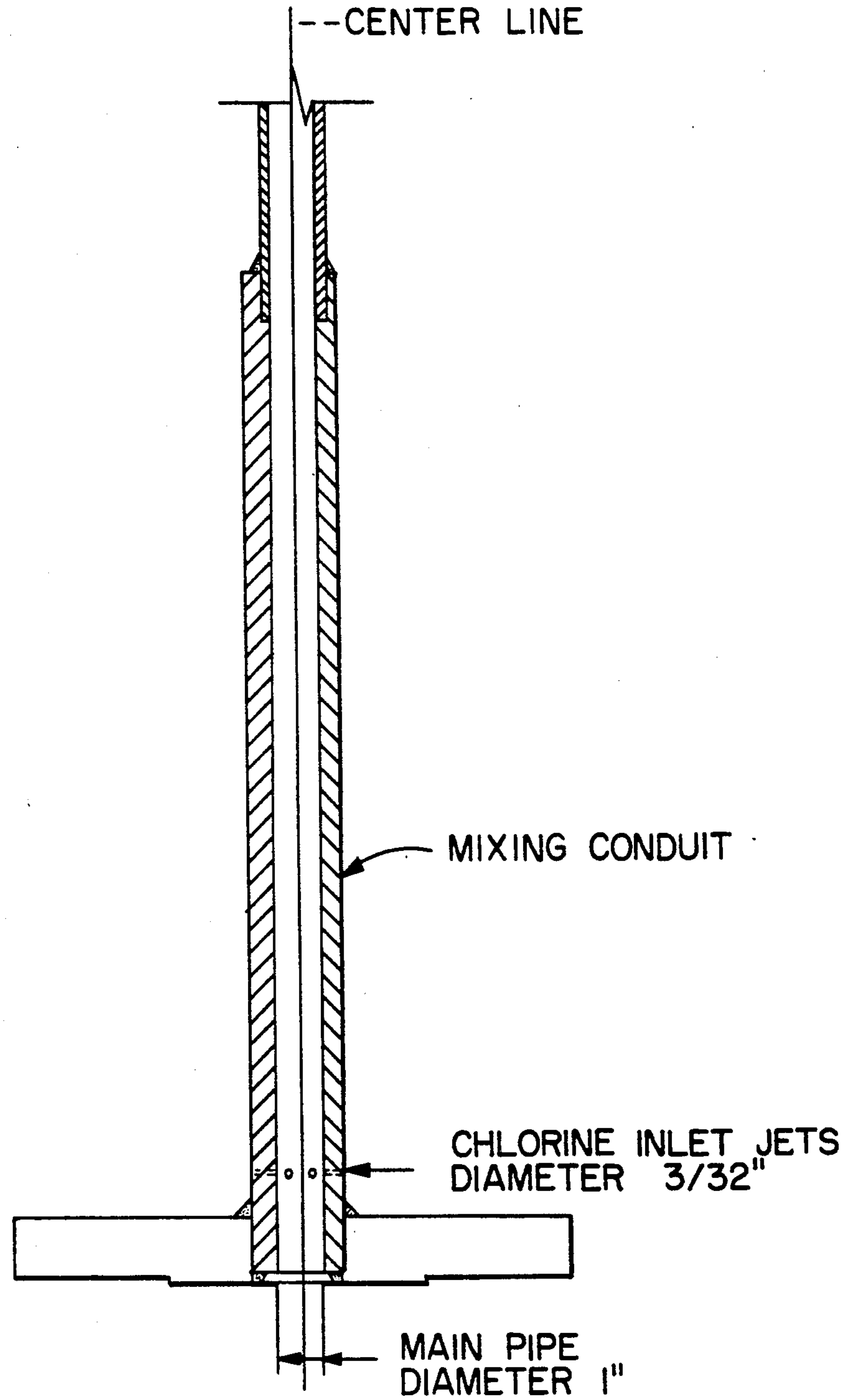
FIG. 2 is a cross-section of the mixer along the length of the main pipe.

Applicants' invention comprises a process for rapidly mixing ethane and chlorine gases such that complete mixing occurs within two pipe diameters after initial contact of the gases. This invention concerns itself with the mixing of ethane and chlorine gases under such conditions that the mixture of the gases would obtain, without any heat due to chemical reaction, a temperature of approximately 225° C. or higher after mixing. Chlorine decomposes to form radicals which initiate the reaction between chlorine and ethane. Although radicals are detectable at lower temperatures, by the time chlorine reaches a temperature of 225° C., the radical concentration becomes appreciable. Accordingly, Applicants' process for mixing chlorine and ethane is not designed for chlorine temperatures higher than approximately 225° C., since such a chlorine stream would contain a high enough concentration of free radicals that there would be inadequate time to effect proper mixture before side reactions occurred. Similarly, one does not wish to have ethane temperatures greater than approximately 650° C. since this temperature is so close to the pyrolysis temperature of ethane that upon mixing with chlorine gas, it is difficult to prevent pyrolysis side reactions. Hereinafter, the term "hot ethane" shall mean ethane of a temperature less than 650°.C. such that when mixed with the chlorine, in Applicants' process, the temperature of the mixture would be approximately 225° C. or above. Although mixing is complete within 2 pipe diameters, it is important that the path between the mixer and the reactor be as smooth as possible. Side reactions that form carbon may be initiated at flow pattern disturbances. This is an important factor only for a short time after mixing. We have found that a smooth conduit of about 10 or more pipe diameters is adequate to avoid this difficulty. Mixers with insufficient conduit length are illustrated in Comparative Examples 3 and 4.

The gas mixer used in Applicants' invention consists of a pipe through which ethane gas flows to the injection region. The injection region is a pipe, called the main pipe, of substantially circular cross section that is pierced by four or more jets through which the chlorine gas is conducted into the main pipe. The use of eight jets is preferred. The jets are distributed substantially evenly about the circumference of the main pipe. The angle between the axis of each jet and the line from the center point of the main pipe to the point where the axis of each jet makes contact with the inside surface of the main pipe, ranges between about 30°–45°.

The range of molar ratios of chlorine to ethane that can be mixed using the process of Applicants' invention is from about 1:40 to about 3:1. At chlorine to ethane ratios below about 1:40 it is difficult to fabricate chlorine jets sufficiently small to achieve the velocities required at such low volume flows. Beyond a chlorine to ethane ratio of about 3:1 it is difficult to construct a mixer that allows such volumes of chlorine without exceeding the velocity limitations of Applicants' invention.

If only four jets are selected, it is important that the angle be somewhat less than 45°. The reason for this is that the configuration of the mixer should be such that the gas stream from a jet strikes the gas stream from another jet before it hits the wall of the pipe.

It is preferred that the jets be small in comparison to the size of the main pipe. The ratio of the main pipe diameter to the jet diameter should be in about the range of 21:1 to 8:1. Our preferred embodiment is to use a main pipe of 1" inside diameter with jets ranging in size from 3/64 of an inch to ⅛ of an inch. In order to assure good mixing, the velocity of the chlorine in the jets should be higher than the velocity of the ethane in the main pipe. The ratio of chlorine velocity to ethane velocity should fall approximately in the range of 1.5:1 to 3.5:1. The preferable range of chlorine to ethane velocity is 2:1 to 3:1.

In Applicants' process for mixing ethane and chlorine, both the ethane and chlorine must be moving at sufficient velocity to establish conditions of turbulence. The Reynolds number is a standard method for measuring the degree of turbulence in a flowing gas stream. It is related to the pressure, velocity, and viscosity of the gas. The Reynolds number increases with increasing gas velocity. The definition of the Reynolds number, and its method of calculation are well known to those skilled in the art. In Applicants' process, each gas stream must have a minimum Reynolds number of 10,000. Higher velocities than those required to produce a Reynolds number of 10,000 may be employed, provided that the velocity of either the ethane or chlorine gas streams, as well as the velocity of the combined stream after introduction of the chlorine, not exceed the speed of sound in the gas under the conditions in question. If the velocity of any gas stream exceeds the speed of sound, in that medium, a shock wave would be created which would actually prevent proper mixing.

The jets are distributed substantially evenly around the main pipe and preferably are substantially in the same plane, which plane is substantially perpendicular to the long axis of the main pipe. If it is not possible to place the jets in the same plane, some jets may be placed in planes substantially parallel to the original plane. The vertical displacement between an two groups of jets should be about one jet diameter. There should be four or more jets in any given plane and within the plane they should be placed substantially evenly around the main pipe. Whether the jets are in one plane or more planes, the axis of each jet is substantially perpendicular to the axis (axis down the center) of the main pipe. There is no conceptual limit on the number of jets or the planes containing them, provided that all the other requirements of the invention are met. Thus, for example, the number of jets is limited by the requirement that all gases must be in turbulent flow, and by the requirement of a certain size ratio between the main pipe and the jets. The method of placement of the jets assures that the stream from each jet will strike and interact with at least two other jet streams. In other words, the jets do not behave independently, but rather interact with each other and with the gas in the main pipe.

The mixer and the pipes leading to it, and from it, should be constructed from suitable materials. Suitable materials are those that do not react with chlorine, and that can tolerate the thermal stress of such a high temperature process. Materials that are suitable for use in high temperature chlorination processes are suitable for use here. For example, high nickel alloys such as Hastelloy, Inconel, and monel are all suitable for construction of Appliants'mixer. In addition, mixers prepared from other materials can be used if they are lined with an inert material such as graphite, alumina, silicon carbide, or other inert material suitable for use in high temperature chlorination reactions.

Optionally, the outside of the mixer can be cooled using methods known to those skilled in the art. We have found that a water jacket around the mixer works well. However, other methods such as cooling fins with forced air are also suitable. If cooling is used, very little cooling is required and it is conducted in such a manner that the temperature loss of the gases being mixed is no more than 5%.

EXAMPLES

Example 1

A mixing device was constructed with a one inch main pipe through which ethane was conducted, and four chlorine jets, evenly spaced around the side of the pipe. The angle between the axis of each jet and the line from the center point of the main pipe to the point where the axis of each jet made contact with the inside surface of the main pipe was 35°. The mixer was lined with graphite, and the area of chlorine injection was water-cooled. Hot ethane was conducted through the main pipe; chlorine was injected at the side jets. The mixer was run for 173 total hours without carbon formation. At two points during the run the temperature was increased. The following chart shows the mixing conditions used during the test.

| | | | |
|---|---|---|---|
| $C_2H_6/Cl_2$ Molar Ratio | 2.6 | | |
| Diameter of Ethane Pipe | 1.0" | | |
| Diameter of Chlorine Pipe | 0.125" | | |
| $Cl_2$ Velocity ft/sec. | 651 | | |
| $C_2H_6$ Velocity ft/sec. | 246 | | |
| $C_2H_6$ Inlet Temp. | 510° C. | 520° C. | 540° C. |
| Hours of Continuous Operation | 123 | 24 | 26 |

Example 2

A mixing device was constructed with a one inch main pipe through which ethane was conducted, and eight chlorine jets, evenly spaced around the side of the pipe. The angle between the axis of each jet and the line from the center point of the main pipe to the point where the axis of each jet made contact with the inside surface of the main pipe was 36°. The mixer was lined with graphite, and the area of chlorine injection was water-cooled. Hot ethane was conducted through the main pipe; chlorine was injected at the side jets. The mixer was run for 168 total hours and the conditions of mixing were changed several times throughout the run. There was also an uncontrolled shutdown after eighty hours of continuous operation. The shutdown was not due to the operation of the mixer, but instead related to extraneous conditions. The brief shutdown and restart did not affect the performance of the mixer.

The following chart shows the mixing conditions used during the test.

| | | | | | |
|---|---|---|---|---|---|
| $C_2H_6/Cl_2$ Molar Ratio | 2.1 | | | | 1.79 |
| Diameter of Ethane Pipe | 1.0" | | | | |
| Diameter of Chlorine Pipe | 0.09375" | | | | |
| $Cl_2$ Velocity ft/sec. | 644 | | | | 693 |
| $C_2H_6$ Velocity ft/sec. | 224 | 220 | 227 | 230 | 221 |
| $C_2H_6$ Inlet Temp. | 500° | 515° | 525° | 535° | 535° |
| Hours of Continuous Operation | 50 | 30 | 40 | 24 | 24 |

Comparative Example 1

Several 90° mixing tees were constructed. In each case, hot ethane was conducted to the mixing tee through the larger pipe. The chlorine was conducted to the mixing tee through the smaller side pipe. The mixing tees were lined with alumina to prevent possible side reactions on the metal surface of the mixer. A wide variety of pipe diameters and relative velocities were explored. In each case, the mixing tee was run until carbon buildup forced shutdown.

The following chart shows the mixing conditions and the hours before shutdown.

| | | | | |
|---|---|---|---|---|
| $C_2H_6/Cl_2$ Molar Ratio | 2.6 | 2.19 | 2.2 | 2.2 |
| Diameter of Ethane Pipe | 2" | 2" | 1.5 | 1.5" |
| Diameter of Chlorine Pipe | 0.75" | 0.75" | 0.5 | 0.50" |
| $Cl_2$ Velocity ft/sec. | 95 | 104 | 233 | 233 |
| $C_2H_6$ Velocity ft/sec. | 80 | 71 | 126 | 126 |
| $C_2H_6$ Inlet Temperature | 488° C. | 466° C. | 460° C. | 460° C. |
| Hours of Operation before shutdown | 13.5 | 5.0 | 5.0 | 10.0 |

Comparative Example 2

A 90° mixing tee was constructed. Hot ethane was conducted to the mixing tee through the larger pipe. The chlorine was conducted to the mixing tee through the smaller side pipe. The mixing tee was lined with graphite to prevent possible side reactions on the metal surface of the mixer. The mixing tee was run until carbon buildup forced shutdown.

The following chart shows the mixing conditions and the hours before shutdown.

| | |
|---|---|
| $C_2H_6/Cl_2$ Molar Ratio | 2.1 |
| Diameter of Ethane Pipe | 1.125" |
| Diameter of Chlorine Pipe | 0.344" |
| $Cl_2$ Velocity ft/sec. | 500 |
| $C_2H_6$ Velocity ft/sec. | 222 |
| $C_2H_6$ Inlet Temp. | 475° C. |
| Hours of Operation before shutdown | 40 |

Comparative Example 3

A mixer was constructed in which ethane traveled in the larger diameter pipe and four evenly spaced, smaller pipes brought chlorine to the mixer. The chlorine pipes were directed at an angle of about 30. to the inner surface of the ethane pipe. The conduit was 1.125" in diameter and was smooth for about 3 pipe diameters. At that point there was an expansion in the conduit to 3 inches. The reactor was shut down due to the formation of carbon at the point where the conduit expanded. There was an uncontrolled shutdown after 45 hours. The shutdown was not due to the operation of the mixer, but instead related to extraneous conditions. The brief shutdown and restart did not affect the performance of the mixer. The mixer was shut down at 77 hours due to coke formation.

The following chart shows the experimental conditions.

| | |
|---|---|
| $C_2H_6/Cl_2$ Molar Ratio | 2.0 |
| Diameter of Ethane Pipe | 1.125" |
| Diameter of Chlorine Pipe | 0.156" |
| $Cl_2$ Velocity ft/sec. | 620 |
| $C_2H_6$ Velocity ft/sec. | 222 |
| $C_2H_6$ Inlet Temp. | 490° C. |
| Hours of Operation before shutdown | 77 |

Comparative Example 4

A mixer was constructed in which ethane traveled in the larger diameter pipe and four evenly spaced, smaller pipes brought chlorine to the mixer. The mixing pipe was less than 1 pipe diameter in length. The chlorine pipes were directed at an angle of about 35. to the inner surface of the ethane pipe. The reactor was shut down due to the formation of carbon.

The following chart shows the experimental conditions.

| | |
|---|---|
| $C_2H_6/Cl_2$ Molar Ratio | 1.9 |
| Diameter of Ethane Pipe | 1.0" |
| Diameter of Chlorine Pipe | 0.125" |
| $Cl_2$ Velocity ft/sec. | 760 |
| $C_2H_6$ Velocity ft/sec. | 210 |
| $C_2H_6$ Inlet Temp. | 500° C. |
| Hours of Operation before shutdown | 24 |

Comparative Example 5

A mixer was constructed in which the ethane was conducted to the mixer through a larger pipe and four evenly spaced pipes brought chlorine to the mixer. The mixer was lined with graphite to prevent possible side reactions on the metal surface of the mixer. The chlorine gas inlets were directed toward the center line of the ethane pipe. The chlorine pipes were slanted so that the chlorine gas stream was not directed perpendicular to the direction of the ethane gas stream, but rather made an angle of 45° to the ethane gas stream. The slant was in a forward direction; that is, in the direction of the ethane gas stream.

The following chart shows the results.

| | |
|---|---|
| $C_2H_6/Cl_2$ Molar Ratio | 1.9 |
| Diameter of Ethane Pipe | 1.0" |
| Diameter of Chlorine Pipe | 0.125" |
| $Cl_2$ Velocity ft/sec. | 760 |
| $C_2H_6$ Velocity ft/sec. | 210 |
| $C_2H_6$ Inlet Temp. | 500° C. |
| Hours of Operation before shutdown | 0.13 |

Comparative Example 6

A mixer was constructed in which ethane was conducted to the mixer in a larger pipe and chlorine was conducted to the mixer through eight evenly spaced pipes. The chlorine pipes were directed toward the center line of the main pipe. The axes of the chlorine pipes intersected with the center line of the ethane pipe at a point near the end of the mixing zone. The chlorine pipes were not directed perpendicularly to the direction of the ethane gas stream, but were, rather, directed at an angle of 60° to the direction of ethane flow. The slant of the chlorine pipes was in the direction of the ethane stream. The reactor was prepared from Inconel metal.

The results are shown in the following chart.

| | |
|---|---|
| $C_2H_6/Cl_2$ Molar Ratio | 1.9 |
| Diameter of Ethane Pipe | 1.0" |
| Diameter of Chlorine Pipe | 0.125" |
| $Cl_2$ Velocity ft/sec. | 760 |
| $C_2H_6$ Velocity ft/sec. | 210 |
| $C_2H_6$ Inlet Temp. | 500° C. |
| Hours of Operation before shutdown | 2 |

Comparative Example 7

A fritted glass mixer was constructed. The ethane was conducted to the mixer through a 25 mm glass tube. The ethane stream was forced through a fritted glass plate. Immediately above the fritted glass plate, chlorine was passed to the mixer through an 8 mm injection tube. At ethane/chlorine feed ratios of 1.1 and 2, carbon formation was a serious problem at any ethane temperature above 200° C. A second fritted mixer was constructed which varied from the first in that the pipe through which the ethane flowed was 35 mm, and the chlorine was conducted to the mixer through a 1 mm tube. The chlorine inlet was directed toward the center of the ethane pipe, and at an angle downward of 15°. This mixer configuration also resulted in severe carbon formation under the test conditions.

Comparative Example 8

A venturi mixer was constructed. The ethane pipe was ⅜" I.D. and was necked down to a throat of approximately 5/16" I.D. At the throat a 6 mm chlorine inlet pipe entered the mixer. At ethane to chlorine feed ratios of 1.1 and 2, carbon formation became a serious problem at any ethane temperature above 200° C.

Comparative Example 9

A coaxial flow reactor was constructed. This reactor consisted of a 25 mm I.D. ethane pipe. Inside this tube was a second tube of approximately 10 mm I.D. through which chlorine gas traveled. The chlorine tube was drawn to a small point and the gases mixed at a neck-down point in the main pipe of approximately 5 mm I.D. Carbon formation was a serious problem at any ethane temperature above 200° C.

We claim:

1. A process for mixing hot ethane with chlorine which comprises the steps of

A. conducting hot ethane at a velocity less than the speed of sound, such that the Reynolds number for said ethane stream is at least 10,000, to a mixer that consists essentially of a main pipe of substantially circular cross section through which said hot ethane flows, pierced by four or more evenly spaced jets, through which said chlorine flows into said main pipe, said jets being directed in a manner such that the angle between the axis of each jet and a line from the center point of the main pipe to the point where the axis of each jet makes contact with the inside surface of the main pipe is between about 30° and about 45°, and the axis of each jet is substantially perpendicular to the axis of said main pipe;

B. introducing said chlorine gas into said mixer through said jets at a velocity less than the speed of sound, such that the Reynolds number of said chlorine gas is at least 10,000;

C. allowing said chlorine and ethane gases to flow through a smooth conduit of the same diameter as said main pipe, with a length at least 10 times the diameter of said main pipe, at a velocity less than the speed of sound, provided that said ratio of said main pipe diameter to said jet diameter is about 21:1 to 8:1, and further provided that the ratio of said chlorine velocity to said ethane velocity is approximately 1.5:1 to 3.5:1.

2. A process according to claim 1 in which said main pipe is pierced by four jets through which said chlorine flows.

3. A process according to claim 2 wherein the ratio of said main pipe diameter to said jet diameter is 15:1 to 8:1.

4. A process according to claim 3 in which the ratio of the chlorine to ethane velocity is 2:1 to 3:1.

5. A process according to claim 4 wherein the angle between said axis of each jet and a line from said center point of said main pipe to a point where said axis of each jet makes contact with the inside surface of said main pipe is between 30° and 40°.

6. A process according to claim 1 in which said main pipe is pierced by eight jets through which said chlorine flows.

7. A process according to claim 6 wherein the ratio of said main pipe diameter to said jet diameter is 15:1 to 8:1.

8. A process according to claim 7 in which the ratio of the chlorine to ethane velocity is 2:1 to 3:1.

9. A process according to claim 8 wherein the angle between said axis of each jet and a line from said center point of said main pipe to a point where said axis of each jet makes contact with the inside surface of said main pipe is between 30° and 40°.

10. A process according to claim 1 with the additional step of cooling the mixer.

11. A process according to claim 10 in which said main pipe is pierced by four jets through which said chlorine flows.

12. A process according to claim 11 wherein the ratio of said main pipe diameter to said jet diameter is 15:1 to 8:1.

13. A process according to claim 12 in which the ratio of said chlorine to ethane velocity is 2:1 to 3:1.

14. A process according to claim 13 wherein the angle between said axis of each jet and a line from said center point of said main pipe to a point where said axis of each jet makes contact with the inside surface of said main pipe is between 30° and 40°.

15. A process according to claim 10 in which said main pipe is pierced by eight jets through which said chlorine flows.

16. A process according to claim 15 wherein the ratio of said main pipe diameter to said jet diameter is 15:1 to 8:1.

17. A process according to claim 16 in which the ratio of said chlorine to ethane velocity is 2:1 to 3:1.

18. A process according to claim 17 wherein the angle between said axis of each jet and a line from said center point of said main pipe to a point where said axis of each jet makes contact with the inside surface of said main pipe is between 30° and 40°.

19. A process according to claim 1 wherein there are eight or more of said jets placed in two or more substantially parallel planes, provided that there are at least four jets in each plane.

* * * * *